United States Patent [19]
Robinson et al.

[11] Patent Number: 5,808,009
[45] Date of Patent: Sep. 15, 1998

[54] METHOD OF AFFINITY PURIFYING ANTIBODIES

[75] Inventors: Michael Robinson; Thomas Russell Gustad; Steven Wayne Meinhardt, all of Fargo, N. Dak.

[73] Assignee: North Dakota State University Research Foundation, Fargo, N. Dak.

[21] Appl. No.: 710,845

[22] Filed: Sep. 23, 1996

[51] Int. Cl.$^6$ .............................. A23J 1/00; C07K 16/00
[52] U.S. Cl. ................ 530/413; 530/412; 530/387.1; 530/388.1; 530/388.2; 530/388.6
[58] Field of Search ................................ 530/413, 412, 530/387.1, 388.1, 388.2, 388.6

[56] References Cited

FOREIGN PATENT DOCUMENTS 9011086 4/1990 WIPO .

OTHER PUBLICATIONS

Robinson et al. (1994) Cellular Immunology vol. 158, 157–166.
England et al. (1990) Methods in Enzymology vol. 182, 285–300.
Cuatrecasas et al (1990) Methods in Enzymology vol. 22, 345–385.

*Primary Examiner*—Paula K. Hutzell
*Assistant Examiner*—Khalid Masood
*Attorney, Agent, or Firm*—David A. Lingbeck

[57] ABSTRACT

The present invention relates to a method of affinity purifying antibodies consisting of the following steps: A) homogenizing Helminth parasite worms forming a mixture; B) incubating the mixture of adult Helminth parasite worm homogenate with pre-swelled CNBr-activated Sepharose 4B in coupling buffer; C) first washing the mixture with blocking buffer; D) second washing the mixture with acetate buffer and coupling buffer; E) third washing the mixture with Phosphate Buffered Solution; F) pouring the mixture into a chromatography column; G) allowing the mixture to settle; H) first passing, by gravity, a solution of saturated ammonium sulfate precipitated antibodies in loading buffer through the chromatography column; I) second passing, by gravity, loading buffer through the chromatography column until thoroughly washed; and J) second passing, by gravity, chromatography column elution buffer through the chromatography column which functions to remove and the purified antibodies.

19 Claims, 4 Drawing Sheets

METHOD OF AFFINITY PURIFYING ANTIBODIES

BACKGROUND OF THE INVENTION

The present invention relates to a method of affinity purifying antibodies utilizing homogenized Helminth Parasite worms particularly of the Heligmosomoides species.

DESCRIPTION OF THE PRIOR ART

*Heligmosomoides polygyrus* is a nematode parasite of mice, where the adult stages exist as a chronic infection in the duodenum of the host. In most strains of mice, a conspicuous feature of infections with *H. polygyrus* is a marked serum hypergammaglobulinemia, which consists largely of immunoglobulins of the IgG1 subclass. This raised IgG1 has been demonstrated to be most prominent in immunized animals, and there is data to indicate that these antibodies have some host protective qualities. However, raised serum IgG1 is also a marked feature of a primary or chronic infection with *H. polygyrus*, and the function of the immunoglobulin produced under these circumstances has been disputed for a number of years.

Studies have clearly shown that primary infection IgG1 has no ability to passively transfer immunity to naive animals, although it has been postulated that these antibodies are probably host protective, but at low specific. However, there appears to be little substantial evidence for any clear host protective role for IgG1 produced by a primary infection. Nevertheless, there are results showing that serum IgG1 levels do correlate with a strain's ability to resist a primary infection with *H. polygyrus*, but the same group, when looking within strains, have found little correlation between IgG1 levels in individual mice.

In contrast, some workers have postulated that rather than being host protective, IgG1 produced during a primary infection may actually block host protective immune responses. More recently, still further opinion has emerged that IgG1 produced by mice infected with *H. polygyrus*, appears to have no role to play in acquired immunity to the parasite. Therefore, there are extensive, but conflicting, data about the role of IgG1 produced during infections with *H. polygyrus*. Some groups suggest that this immunoglobulin aids the parasite, some suggest that it is irrelevant, and some suggest that it aids the host. The interactions between the parasite and IgG1 from naive mouse splenocytes. Upon analysis, however, the immunoglobulin produced by this stimulation of mouse lymphocytes showed little or no specificity for the stimulating AWH, which leads to the question of a physiological role for this antibody. Interestingly, there is great deal of published information showing that many helminth parasites are able to bind host serum proteins, and recently Enriquez et al. have shown that *H. polygyrus* can bind to IgE, without utilizing the Fab portion of the immunoglobulin molecule. As these facts might be relevant to the possible role of IgG1 in *H. polygyrus* infections, the ability of *H. polygyrus* to non-specifically bind to mouse IgG1 was investigated. It is postulated that the parasite is able to bind the mouse IgG1 to its own proteins and this is a means by which the parasite modulates the host immune response. Furthermore, if the parasite can bind IgG1 non-specifically, this mechanism could be utilized to extract IgG1 from complex mixtures.

Numerous innovations for purification of antibodies have been provided in the prior art that are adapted to be used. Even though these innovations may be suitable for the specific individual purposes to which they address, they would not be suitable for the purposes of the present invention as heretofore described.

SUMMARY OF THE INVENTION

The present invention relates to a method of affinity purifying antibodies. More particularly, the present invention relates to a method of affinity purifying antibodies[13] utilizing homogenized worms of helminth parasites of the Heligmosomoides species.

Monoclonal antibodies (MoAb) are an invaluable tool in many aspects of modern life. They are used in disease diagnosis in medical, veterinary and agricultural fields, as well as being increasingly utilized in actual disease treatment.

For a variety of reasons, by far the most important animal used to produce MoAb is the laboratory mouse, which generally produces MoAb of IgM, IgG1, IgG2a, IgG2b, IgC3 and IgA isotypes. Of these isotypes, IgG1 is the one most frequently found and hence the most important. Monoclonal antibodies can be produced in the animal, as ascites, or in culture, but in both cases the immunoglobulins produced are contaminated with extraneous proteins and these must be removed during purification. It has been discovered that certain strains of *Staphylococcus aureus* and Streptococcus sp produces products which non-specifically bind to mammalian immunoglobulin and these products: called Protein A and Protein G, respectively, are utilized commercially for the purification of monoclonal antibodies. The accepted way of doing this is to use affinity chromatography, where the fluid containing the mouse immunoglobulin is passed through a chromatographic column in which either Protein A or Protein G have been attached to the matrix. This contaminating proteins are washed through the column, while the bound immunoglobulin can be subsequently eluted from the column using a suitable buffer.

The problems with the established techniques are that:
1) Protein A binds rather poorly to mouse IgG1 at physiological pH and at extreme pH s there is a risk of denaturing the antibody.
2) Conversely, Protein G binds so tightly to mouse IgG1 that elution causes damage to the antibody.

Innovations within the prior art are rapidly being exploited in the field of purification of antibodies.

The types of problems encountered in the prior art are purification of antibodies is often difficult and expensive.

In the prior art, unsuccessful attempts to solve this problem were attempted namely: binding antibodies to capturing molecules such as Protein A. However, the problem was solved by the present invention because by utilizing the Helminth Parasite homogenate, binding of the antibodies occurs yet it allows release therefrom relatively easily which results in a higher yield of viable antibodies and thus reduced cost of purification.

The present invention went contrary to the teaching of the art which teaches the use of well known standard antibody capturing molecules.

The present invention solved a long felt need for an inexpensive, simple, rapid high yielding antibody purification technique.

The novel features which are considered characteristic for the invention are set forth in the appended claims. The invention itself, however, both as to its construction and its method of operation, together with additional objects and advantages thereof, will be best understood from the following description of the specific embodiments when read and understood in connection with the accompanying drawings.

BRIEF LIST OF REFERENCE NUMERALS UTILIZED IN THE DRAWINGS

110—method of affinity purifying antibodies (110)
112—Heligmosomoides species worms forming a mixture
114—incubating (114) the mixture of adult Heligmosomoides species worm homogenate with pre-swelled CNBr-activated Sepharose 4B in coupling buffer
116—first washing (116) the mixture with blocking buffer
118—second washing (118) the mixture with acetate buffer and coupling buffer
120—third washing (120) the mixture with Phosphate Buffered Solution
122—pouring (122) the mixture into a chromatography column
124—allowing (124) the mixture to settle.
126—first passing (126), by gravity, a solution of saturated ammonium sulfate precipitated antibodies in loading buffer through the chromatography column
128—second passing (128), by gravity, loading buffer through the chromatography column until thoroughly washed
130—second passing (130), by gravity, chromatography column elution buffer through the chromatography column which functions to remove and the purified antibodies
132—quantifying (132) the purified antibodies by absorption
134—diluting (134) the purified antibodies and removing excess NaCl by centrifugation
136—isolating (136) the purified antibodies

DESCRIPTION OF THE PREFERRED EMBODIMENTS

Figure 1:
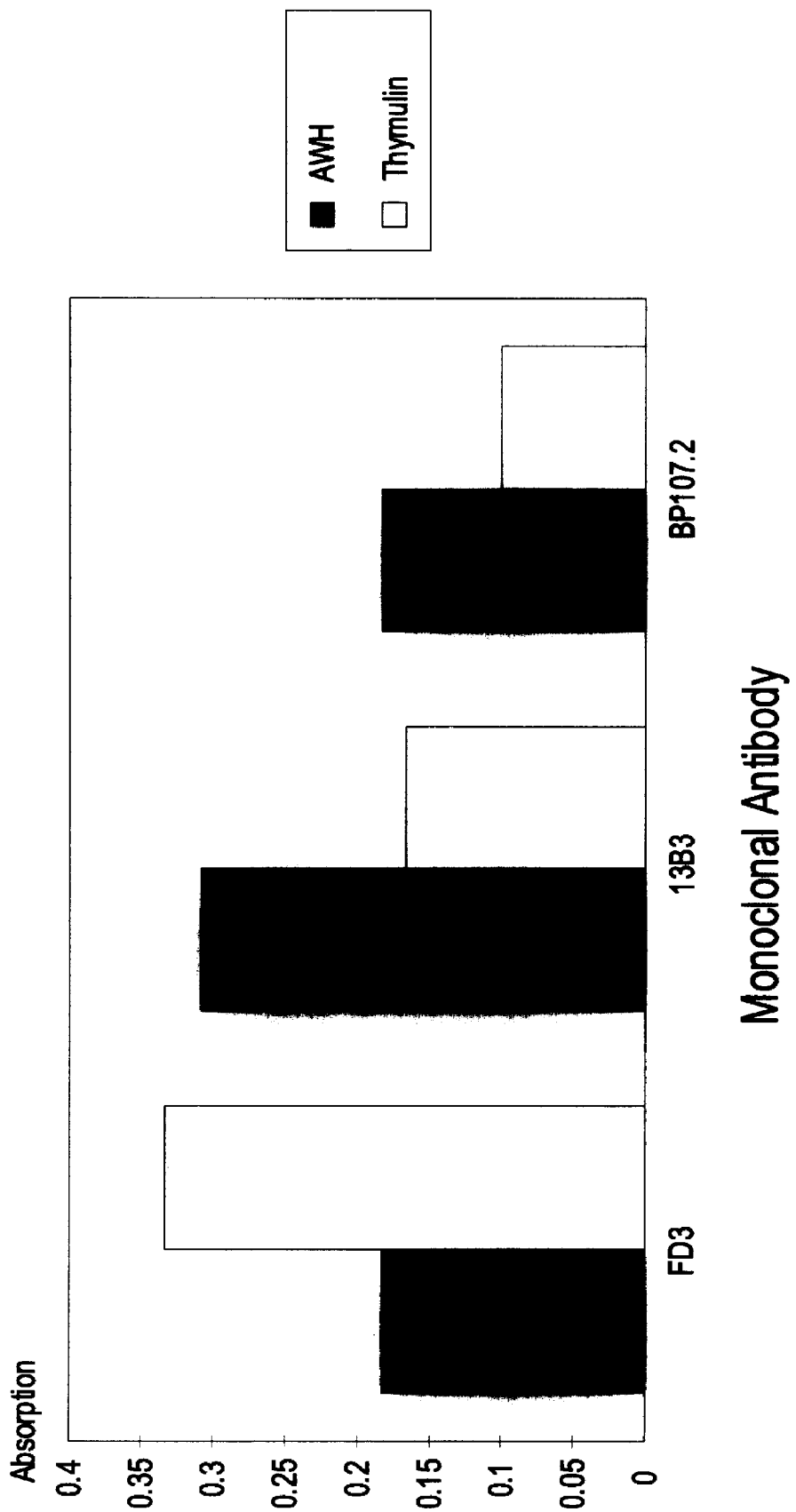
FIG. 1 is a diagrammatic representation of the ELISA to indicate the specificity of MoAb FD3, 13B3 and BP107.2 for thymulin and H. polygyrus AWH.

Referring to FIG. 1 is a diagrammatic representation of an ELISA to indicate the specificity of MoAb FD3, 13B3 and BP107.2 for thymulin and H. polygyrus AWH. Readings for PBS/Tween, only, were 0.108 and 0.122 (AWH and thymulin, respectively).

Initial characterization of the MoAb to be used in the affinity column, was by determining whether FD3, specific for mouse thymulin, cross reacted with AWH. FIG. 1 indicates that both MoAb 13B3 (anti-AWH) and FD3 bound specifically, but that cross reactivity was low. MoAb BP107.2 (anti-mouse Ia) was also included in this assay as a negative control, and bound poorly to both antigens. Results of FIG. 1 are for 1/100 dilution of MoAb, but similar binding characteristics were observed at other dilutions.

Figure 2A:
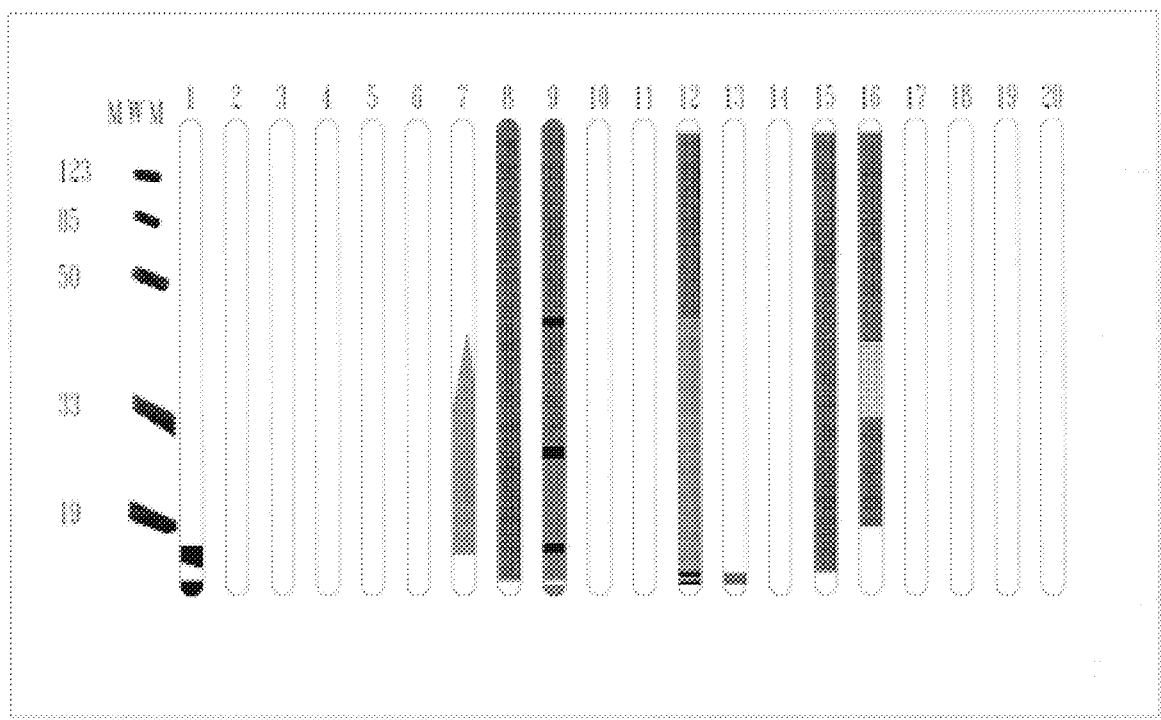
FIG. 2A is a Western (protein) blot to show the binding of MoAb to individual proteins of H. polygyrus AWH with the NMS mouse serum omitted from blocking buffer.
Figure 2B:
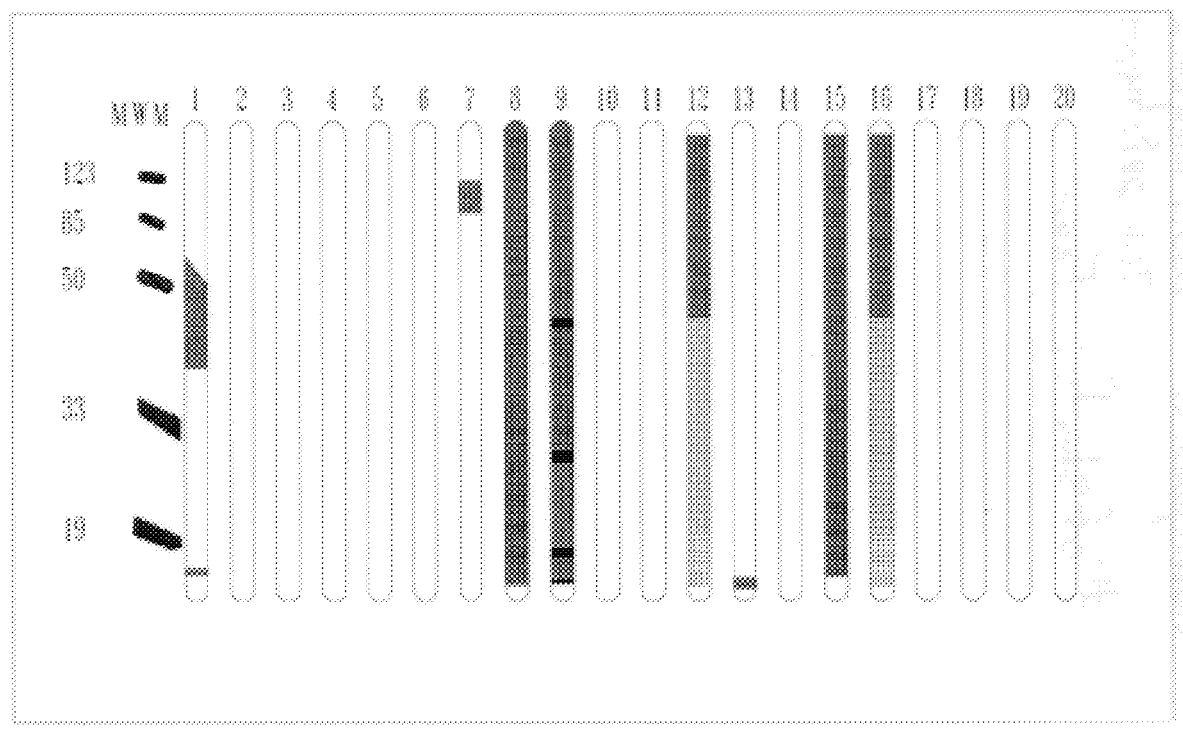
FIG. 2B is a Western (protein) blot to show the binding of MoAb to individual proteins of H. polygyrus AWH with the addition of NMS to the blocking buffer.

Referring to FIG. 2A and FIG. 2B which are Western (protein) blots to show the binding of MoAb to individual proteins of H. polygyrus AWH with the omission and addition, respectively, of NMS to the blocking buffer. The blocking buffers used were a. TBS/3% BSA. b. TBS/3% BSA/1% NMS. Antibodies and lanes were: 1=5B2 (100 μg/ml); 2=FD3 (10 μg/ml); 3=FD3 ( )100 μg/ml); 4=NMS (1:100); 6=Buffer only; 7=HpD (100 μg/ml); 8=6C2 (100 μg/ml); 9=HIS (1:100); 10=BP107.2 (100 μg/ml); 11=25-5-16S (100 μg/ml); 12=9A3 (100 μg/ml); 13=13B3 (100 μg/ml); 14=EA3 (100 μg/ml); 15=8B3 (100 μg/ml); 16=12A4 (100 μg/ml); 17=1B7.11 (100 μg/ml); 18=1A6 (100 μg/ml); 19=NMS (1:100); 20=blank.

The present invention describes a new technique which uses a product from the nematode *Heligmosomoides polygyrus*. When bound to a suitable matrix, such as cyanogen bromide (CNBr) activated Sepharose 4B, this product will readily bind to mouse IgG1 at physiological pH, and can then be eluted from the column using saturated NaCl.

This technique uses commercially available materials and established methodology and the only limiting factor is the availability of parasite material. The immunoglobulins produced are stable, still retain their original specificity, and after removal of the elution buffer, are ready to use.

MICE

During research utilizing the present invention, BALB/c mice were bred and maintained in the Department of Veterinary and Microbiological Sciences, NDSU. Mice were a minimum of two months old at the time of experimentation.

THE PARASITE

The production and maintenance of *Heligmosomoides polygyrus* was in outbred Swiss Webster mice.

ANTIGEN

Adult *H. polygyrus* worms were removed from the intestine of mice using a modified Baermann technique. Worms were washed repeatedly in distilled water and a protinin was added at 0.1U/ml of worms, prior to homogenization using a ground glass tissue homogenizer. The homogenate was centrifuged at 16,600×g for 30', at 4° C., then the supernatant was removed and sterilized using a 0.2 μm filter. The protein concentration of the resultant *H. polygyrus* adult worm homogenate (AWH) was assayed using a BCA assay, with BSA as the standard.

MONOCLONAL ANTIBODIES

Monoclonal antibodies (MoAb) 9A3, 13B3, 12A4, 5B2, HpD (all IgG1), 8B3, 6C2 (all IgM), to *H. polygyrus* AWH; MoAb EA3, FD3 (all IgG1 ) to mouse thymulin; MoAb 1A6 (IgM, to KLH, were produced in BALB/c mice at NDSU, according to accepted methodology. All other MoAb were produced from hybridomas purchase from American Type Tissue Culture (ATTC). The hybridomas 1B7.11 and 25-5-16S produce mouse IgG1 MoAb specific for 2,4,6 Trinitrophenyl (TNP) and IgM specific for mouse Ia respectively. Hybridoma BP 107.2 produces a mouse IgG3 MoAb specific for mouse Ia.

All MoAb were produced in cell culture and concentrated using 45% saturated ammonium sulfate (SAS), followed by dialysis. *H. polyrgyrus*-specific, hyper immunized mouse serum (HIS) was produced in BALB/c that has been immunized during the production of the anti-*H. polygyrus* MoAb. Normal mouse serum (NMS) was pooled from several naive BALB/c mice, bred in the mouse colony at NDSU.

As thymulin is only nine amino acids long (EAKSQGGSD), a thymulin-BSA conjugate was used as the antigenic stimulant and a thymulin-KLH (keyhole limpet hemocranin) conjugate was used to test for the specificity of the monoclonal antibodies produced. The thymulin-specific MoAb used in these studies do not bind to KLH in isolation. The specificity of the hybridomas was tested by ELISA, with AWH or thymulin-KLH as the target antigen.

ELISA

For evaluation of specific immunoglobulin, plates were coated with 100 μg of coating buffer, containing either 10

µg/ml (AWH) or 2 µg/ml (thymulin) of protein, followed by blocking with 3% chicken egg albumin (CEA). SAS precipitated immunoglobulin was then added. Bound antibody was detected using either alkaline phosphatase (AP) conjugated, rabbit anti-mouse IgG and IgM, or by biotinylated goat anti-mouse IgG, with a streptavidin-biotinylated AP complex. The substrate, pNPP (para nitrophenyl phosphate, Sigma), was used according to the manufacturers instructions. The reaction was quantified, by measuring the optical density at 405 nm, using a Biotek microplate reader. SDS-PAGE 10% SDS-PAGE was carried out using Mini-Protean II electrophoresis equipment, according to the manufacturers instructions. Low and high molecular weight markers were purchased from BIO-RAD (TM). Mouse IgG1 and bovine globulin were purchased as indicated. Gels were stained using a silver staining technique, according to published methodology.

WESTERN (PROTEIN) BLOTS 100 µg of *H. polygyrus* AWH was electrophoretically separated on a 10% SDS-PAGE gel, then blotted onto a PVDF (polyvinylidene fluoride) membrane, using Mini-PROTEAN II electrophoresis and blotting equipment, according to the manufacturers instructions. The blot was blocked overnight with tris buffered saline (TBS), containing 3% BSA, with or without 1% NMS, then washed three times, for ten minutes each wash, with TBS/0.2% Tween 20, prior to being transferred to a Mini-PROTEAN II Multi Screen apparatus for probing. The blot was incubated with the appropriate monoclonal antibodies, diluted with TBS/1% BSA, for 1 hour, then washed three times, followed by a 1 hour incubation with AP conjugated goat anti-mouse IgG and IgM polyclonal antibody, diluted 1/5000 with TBS/1% BSA. This was followed by a further three washes. The blot was then removed to a plastic container and washed once in TBS for ten minutes, followed by the addition of BIO-RAD Immuno-Blot color development reagent, BCIP (5-bromo-4-chloro3-indoyl phosphate) and NBT (nitroblue tetrazolim), in DMF (dimethylformamide) for 7 minutes. The reaction was stopped by washing with distilled water. All procedures were carried out at room temperature.

AFFINITY CHROMATOGRAPHY 50 mg of *H. polygyrus* adult worm homogenate (AWH) was incubated overnight with 3g of pre-swelled CNBr-activated Sepharose CL-4B in coupling buffer (0.1M NaHCO3, 0.5M NaCl, pH 8.3). The resulting mixture was then washed repeatedly with blocking buffer (0.2M glycine, pH 8.0), followed by alternative washes with acetate buffer (0.1M sodium acetate, 0.5M NaCl, pH 4.0) and coupling buffer, followed by a final wash with PBS. The AWH/Sepharose mixture was poured into a plastic liquid chromatography column and allowed to settle. A solution of 45% SAS precipitated MoAb, in loading buffer (20 mM MOPS, 20 mM NaCl, pH 7.2) was then allowed to pass through the column, under gravity. The column was washed with loading buffer, followed by the addition of elution buffer (4M NaCl) re remove the purified MoAb. The antibodies removed from the column were quantified, approximately, by absorption at 260 nm and 280 nm, then diluted and the excess NaCl removed by centrifugation, using a Centriprep concentrator.

To assay the antibody eluted from the column, protein fraction were collected, as indicated, and desalted, as required. Protein concentrations were adjusted to 0.5 mg/ml using the formula: 1.55×A280−0.76×A260 (=mg/ml), then their ability to bind to AWH was determined by ELISA, as detailed above.

The second stage of the analysis was to carry out protein blotting of AWH with various antibody preparations, both specific and non-specific for *H. polygyrus* AWH. The blots were carried out using two slightly differing methodologies, with the blocking solution consisting of TBS/BSA, but for one blot, NMS was included also. These two different methodologies produced quite different results, as indicated in FIG. 2A and FIG. 2B. When the NMS mouse serum was omitted from blocking buffer in FIG. 2A, the antibodies bound in discrete bands, as expected. However, with the addition of NMS to the blocking buffer in FIG. 2B, then further bands appeared which were common to all antibody preparations tested. These results indicated that a factor in NMS was binding to AWH proteins, which was then recognized by the goat anti-mouse antiserum of the second antibody. On the assumption that this factor might be mouse IgG1, we produced an affinity column using bound AWH, to determine if this could extract non-specific IgG1 from a semi-purified preparation of MoAb FD3. There were two factors which we wished to ascertain: whether IgG1 would bind to AWH with sufficient affinity to allow it to adhere to the column, but also whether we could then extract the bound IgG1, in a way which would not denature the protein, or adversely affect antibody binding.

A typical elution profile from the affinity column was determined wherein samples were collected in 1 ml units and assayed for protein content, using the formula described above. The protein did bind to the column and was also satisfactorily eluted, when high salt was added to the column. The next step was to determine the specificity of the eluted protein, after the high salt buffer was removed. The ELISA results from pooled fractions from the affinity chromatography, and all fractions contained FD3 antibody, which was still able to bind to the specific antigen. This indicates that none of the steps in the affinity purification denatured the antibody, but also that unbound fraction had considerable amounts of FD3 removed by the affinity purification process.

When the protein produced by affinity chromatography was analyzed by SDS-PAGE, it could be seen that a large part of the bovine albumin (66 kD) which had been in the unfractionated FD3 MoAb, was missing from the bound FD3, but was still at high levels in the unbound FD3. Furthermore, the bound FD3 could be seen to contain immunoglobulin.

The results described herein are of interest from two viewpoints. The first is they demonstrate that the IgG1, which is produced by mice infected with *H. polygyrus*, can bind to the stage of the parasite which exists as a chronic infection within the host. As the specificity of the antibody is plainly not the reason for the binding (FIG. 2A and FIG. 2B), then one must assume that, as with IgE, the binding is not via the Fab region of the immunoglobulin molecule. These results would, therefore, indicate that the non-specific IgG1 produced by AWH, is not merely a by-product of stimulation of mouse lymphocytes, but does in fact interact with the stimulating organism. These data would probably add some credibility to the idea that the IgG1 produced during a primary infection with *H. polygyrus* does not act to benefit the host, but instead could act as an immunological blocking.

The results described here also indicate that the binding sites to which IgG1 adheres, bind BSA, CEA, bovine immunoglobulins, and possibly other proteins. The data from the ELISA indicates that CEA can effectively block non-specific binding of the IgG1 to AWH (FIG. 1), while the protein blots show that blocking the blots overnight with BSA, also does the same thing (FIG. 2A). However, when NMS was added to the blocking buffer, then mouse immunoglobulins were able to bind and the extra bands results (FIG. 2B). Likewise the affinity column was able to bind mouse IgG1, in the presence of other serum proteins, indicating that under the conditions utilized during these experiments, the affinity of AWH for mouse IgG1, is higher than for some other proteins. In regard to this latter point, we have also used the same column to determine if we could extract bovine immunoglobulins from the foetal calf serum contained in the Hybridoma culture medium. Although we could not determine the specificity of these immunoglobulins, we could quantitatively measure them using an ELISA capture assay. We were successful in showing that the affinity column also effectively binds bovine immunoglobulins. This probably accounts for the rather heterogeneous immunoglobulin light chain seen in the bound fraction. Therefore, many serum proteins appear able to non-specifically bind to H. polygyrus AWH, although the evidence here would suggest that the binding affinities, under the conditions utilized here, vary considerably. This would be in accordance with data obtained using Protein A, as the affinity medium.

The second point of interest is of a functionality, because these data show that mouse IgG1 can be successfully isolated, by affinity chromatography, using AWH as the affinity medium. In this study we were not overly concerned with optimizing this procedure, but merely wished to demonstrate its effectiveness. Therefore, further work must be carried out to determine the ideal concentration of proteins and whether other buffer systems might be more suitable. However, we have used this method to successfully purify mouse IgG1 monoclonal antibodies. The methodology is a variation of established procedures, and effectively purifies IgG1 while still maintaining the viability of the immunoglobulin. This has some advantages over Protein A, where buffers with extreme pH are often recommended, and also over Protein G, in which removal of the bound antibody can be difficult.

Interestingly, this ability to bind proteins non-specifically could present problems during some assays. Although effective blocking when carrying out protein blotting and ELISAs should eliminate any false positives, the identification of antigenic proteins by immuno precipitates could easily be affected. Therefore, results describing cross reactivity between monoclonal antibodies and H. polygyrus, may need to be re-examined.

In summary, these results demonstrate that serum proteins, including IgG1, are able to bind non-specifically to H. polygyrus AWH. This binding of IgG1 is competitive and reversible, and can be utilized during affinity chromatography, in order to extract mouse IgG1. It is postulated that the parasite stimulates the host to produce non-specific IgG1, which can then bind to selected parasite proteins, and it is presumed that this mechanism acts to the parasites, rather than the hosts, advantage.

Figure 3:
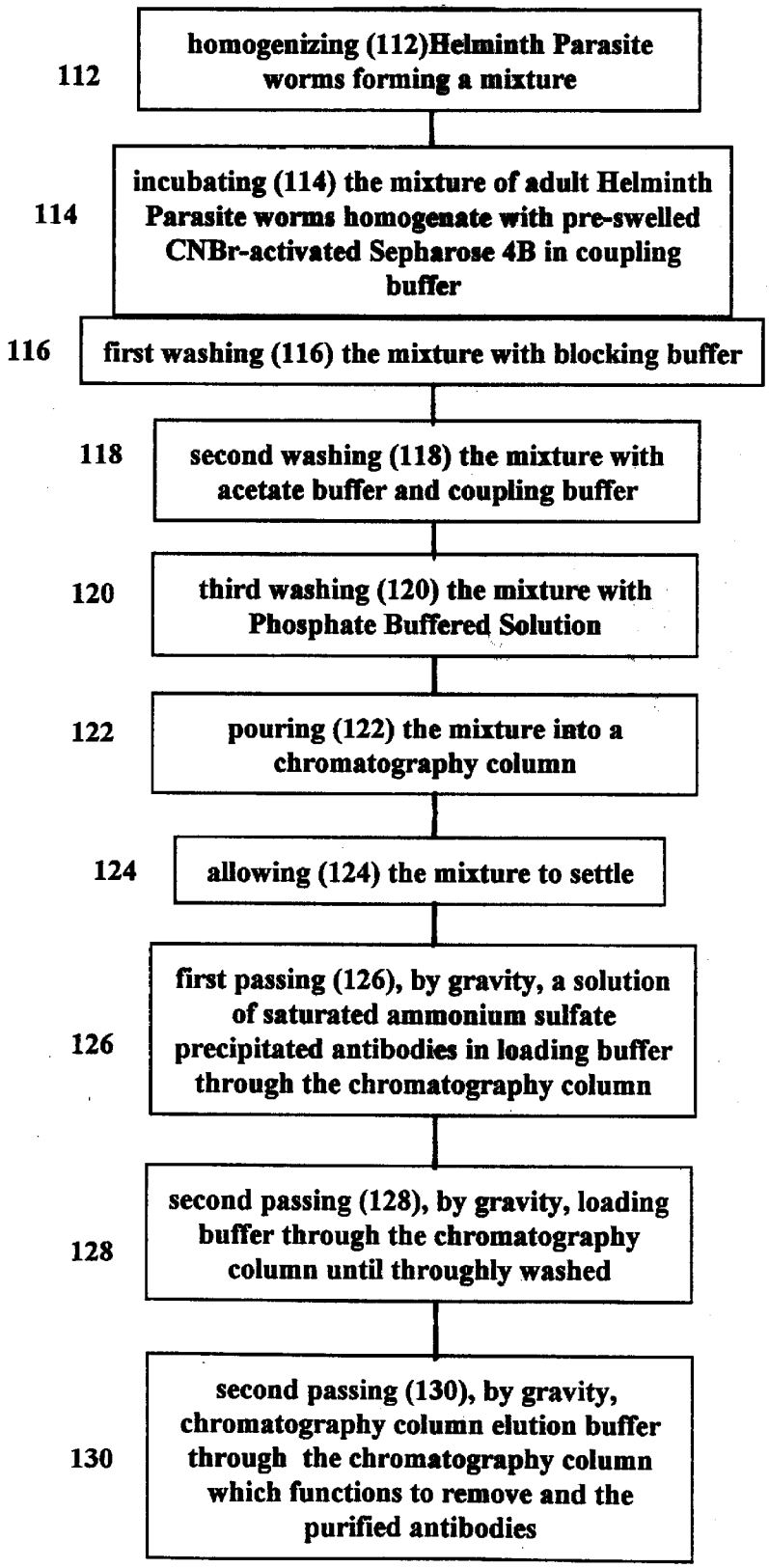
FIG. 3 is a diagrammatic representation of a method of affinity purifying antibodies.

Lastly, referring to FIG. 3 which is a diagrammatic representation of a method of affinity purifying antibodies (110) preferably consisting of the following steps:

A) homogenizing (112) adult H. polygyrus worms;
B) incubating (114) a mixture of 50 mg of adult H. polygyrus worm homogenate with 3 g of pre-swelled CNBr-activated Sepharose 4B in coupling buffer (0.1MNaIl03, 0.5M NaCl, pH 8.0);
C) first washing (116) the mixture with blocking buffer (0.2M glycine, pH 8.0);
D) second washing (118) the mixture with acetate buffer (0.1M sodium acetate, 0.5M NaCl, pH 4.0) and coupling buffer;
E) third washing (120) the mixture with PBS;
F) pouring (122) the mixture into a plastic liquid chromatography column;
G) allowing (124) the mixture to settle;
H) first passing (126) by gravity a solution of 45% SAS (saturated ammonium sulfate) precipitated antibodies, in loading buffer (20 mM MOPS, 20 mM NaCl pH 7.2) through the chromatography column
I) second passing (128) by gravity through the chromatography column loading buffer until thoroughly washed; and
J) second passing (130) by gravity through the chromatography column elution buffer (4M NaCl) which functions to remove the purified antibodies.

The method of affinity purifying antibodies (110) may optionally further consist of the following step:
A) quantifying (132) the purified antibodies by absorption.

The method of affinity purifying antibodies (110) may optionally further consists of the following step:
A) diluting (134) the purified antibodies and removing excess NaCl by centrifugation.

The method of affinity purifying antibodies (110) may optionally further consists of the following step:
A) isolating (136) the purified antibodies. Although the adult H. polygyrus worm is preferable, the method of affinity purifying antibodies (110) may optionally utilize worms selected from a group of species of worms consisting of Heligmosomoides species as well as other Helminth parasites.

The method of affinity purifying antibodies (110) may optionally utilize the adult Heligmosomoides species worm homogenate in a range from 25 mg to 75 mg.

The method of affinity purifying antibodies (110) may optionally utilize the pre-swelled CNBr-activated Sepharose 4B is a range from 1 g to 5 g.

The method of affinity purifying antibodies (110) may optionally utilize the saturated ammonium sulfate in a range of 30% to 60%.

The method of affinity purifying antibodies (110) preferably utilizes monoclonal antibodies. However, heterogeneous antibodies may also be optionally utilized.

The method of affinity purifying antibodies (110) preferably utilizes mammalian antibodies in particular mouse monoclonal antibodies. In addition other antibodies can be utilized which are selected from a group of animals consisting of mammals (ie. human, dog, cat, horse, goat, bovine etc.), birds, and reptiles.

It will be understood that each of the elements described above, or two or more together, may also find a useful application in other types of constructions differing from the type described above.

While the invention has been illustrated and described as embodied in a method of purification of antibodies, it is not intended to be limited to the details shown, since it will be understood that various omissions, modifications, substitutions and changes in the forms and details of the device illustrated and in its operation can be made by those skilled in the art without departing in any way from the spirit of the present invention.

Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention.

This is claimed as new and desired to be protected by Letters Patent is set forth in the appended claims.

What is claimed is:

1. A method of affinity purifying IgG1 antibodies from a mixture comprising the following steps performed in the following order:
   A) homogenizing adult *Heligmosomoides polygyrus* worms to form an adult worm homogenate;
   B) incubating a mixture of adult worm homogenate and pre-swelled CNBr-activated Sepharose 4B in coupling buffer under conditions whereby the adult worm homogenate is coupled to the Sepharose 4B;
   C) washing the worm homogenate-coupled Sepharose 4B obtained in step B with blocking buffer;
   D) washing the worm homogenate-coupled Sepharose 4B with acetate buffer and coupling buffer;
   E) washing the worm homogenate-coupled Sepharose 4B with phosphate buffered solution to obtain Sepharose 4B-coupled worm homogenate;
   F) pouring the Sepharose 4B-coupled worm homogenate obtained in step E into a chromatography column;
   G) allowing the Sepharose 4B-coupled worm homogenate to settle;
   H) passing a solution of saturated ammonium sulfate precipitated antibodies in loading buffer through the chromatography column whereby IgG1 antibodies present in said precipitated antibodies bind non-specifically to said adult worm homogenate;
   I) passing loading buffer through the chromatography column until thoroughly washed; and
   J) passing chromatography column elution buffer through the chromatography column to obtain purified IgG1 antibodies.

2. The method of affinity purifying antibodies as described in claim 1, further comprising the step of quantifying the purified IgG1 antibodies obtained in step J by absorption.

3. The method of affinity purifying antibodies as described in claim 1, further comprising the step of diluting the purified antibodies obtained in step J and removing excess sodium chloride by centrifugation.

4. The method of affinity purifying antibodies as described in claim 1, further comprising the step of isolating the purified antibodies.

5. The method of affinity purifying antibodies as described in claim 1, wherein the adult worm homogenate is in a range from 25 mg to 75 mg.

6. The method of affinity purifying antibodies as described in claim 1, wherein the adult worm homogenate is 50 mg.

7. The method of affinity purifying antibodies as described in claim 1, wherein the pre-swelled CNBr-activated Sepharose 4B is in a range from 1 g to 5 g.

8. The method of affinity purifying antibodies as described in claim 7, wherein the pre-swelled CNBr-activated Sepharose 4B is 3 g.

9. The method of affinity purifying antibodies as described in claim 1, wherein the coupling buffer is 0.1M NaHCO3 and 0.5M NaCl having pH 8.0.

10. The method of affinity purifying antibodies as described in claim 1, wherein the blocking buffer is 0.2M glycine having pH 8.0.

11. The method of affinity purifying antibodies as described in claim 1, wherein the acetate buffer is 0.1M sodium acetate and 0.5M NaCl having pH 4.0.

12. The method of affinity purifying antibodies as described in claim 12, wherein the saturated ammonium sulfate is in a range of 30% to 60%.

13. The method of affinity purifying antibodies as described in claim 1, wherein the saturated ammonium sulfate is 45%.

14. The method of affinity purifying antibodies as described in claim 1, wherein the loading buffer is 20 mM MOPS and 20 mM NaCl having pH 7.2.

15. The method of affinity purifying antibodies as described in claim 1, wherein the chromatography column is a plastic liquid chromatography column.

16. The method of affinity purifying antibodies as described in claim 1, wherein the chromatography column elution buffer is 4M NaCl.

17. The method of affinity purifying antibodies as described in claim 2, wherein the absorption is selected from a group consisting of 260 nm and 280 nm.

18. The method of affinity purifying antibodies as described in claim 1, wherein the antibodies are selected from a group consisting of monoclonal and heterogenous antibody mixtures.

19. The method of affinity purifying antibodies as described in claim 1, wherein the antibodies are selected from a group of animals.

* * * * *